US00RE42497E

(19) United States
(12) Reissued Patent
Wax

(10) Patent Number: US RE42,497 E
(45) Date of Reissued Patent: Jun. 28, 2011

(54) FOURIER DOMAIN LOW-COHERENCE INTERFEROMETRY FOR LIGHT SCATTERING SPECTROSCOPY APPARATUS AND METHOD

(75) Inventor: Adam Wax, Chapel Hill, NC (US)

(73) Assignee: Duke University, Durham, NC (US)

(21) Appl. No.: 12/205,248

(22) Filed: Sep. 5, 2008

Related U.S. Patent Documents

Reissue of:
(64) Patent No.: 7,102,758
Issued: Sep. 5, 2006
Appl. No.: 10/429,756
Filed: May 6, 2003

(51) Int. Cl.
*G01B 9/02* (2006.01)
(52) U.S. Cl. ..... 356/497
(58) Field of Classification Search ..... 356/479, 356/497
See application file for complete search history.

(56) References Cited

U.S. PATENT DOCUMENTS

| | | | | |
|---|---|---|---|---|
| 4,646,722 | A | 3/1987 | Silverstein et al. | |
| 5,386,817 | A | 2/1995 | Jones | |
| 5,489,256 | A | 2/1996 | Adair | |
| 5,534,707 | A | 7/1996 | Pentoney | |
| 5,565,986 | A | 10/1996 | Knuttel | |
| 5,601,087 | A | 2/1997 | Gunderson et al. | |
| 5,643,175 | A | 7/1997 | Adair | |
| 5,771,327 | A | 6/1998 | Bar-Or et al. | |
| 5,930,440 | A | 7/1999 | Bar-Or | |
| 5,956,355 | A * | 9/1999 | Swanson et al. | 372/20 |
| 6,002,480 | A * | 12/1999 | Izatt et al. | 356/479 |
| 6,091,984 | A | 7/2000 | Perelman et al. | |
| 6,134,003 | A * | 10/2000 | Tearney et al. | 356/479 |
| 6,174,291 | B1 | 1/2001 | McMahon et al. | |
| 6,233,373 | B1 | 5/2001 | Askins et al. | |
| 6,263,133 | B1 | 7/2001 | Hamm | |
| 6,404,497 | B1 | 6/2002 | Backman et al. | |
| 6,501,551 | B1 | 12/2002 | Tearney et al. | |
| 6,564,087 | B1 | 5/2003 | Pitris et al. | |
| 6,624,890 | B2 | 9/2003 | Backman et al. | |
| 6,697,652 | B2 | 2/2004 | Georgakoudi et al. | |
| 6,775,007 | B2 | 8/2004 | Izatt et al. | |
| 6,847,456 | B2 | 1/2005 | Yang et al. | |
| 6,853,457 | B2 | 2/2005 | Bjarklev et al. | |
| 6,863,651 | B2 | 3/2005 | Remijan et al. | |
| 6,879,741 | B2 | 4/2005 | Salerno et al. | |
| 7,061,622 | B2 | 6/2006 | Rollins et al. | |
| 7,079,254 | B2 | 7/2006 | Kane et al. | |
| 7,102,758 | B2 | 9/2006 | Wax | |
| 7,355,716 | B2 | 4/2008 | de Boer et al. | |
| 7,366,372 | B2 | 4/2008 | Lange | |
| 7,391,520 | B2 | 6/2008 | Zhou et al. | |
| 7,417,740 | B2 | 8/2008 | Alphonse et al. | |
| 7,428,050 | B2 | 9/2008 | Giakos | |
| 7,428,052 | B2 | 9/2008 | Fujita | |
| 7,616,323 | B2 | 11/2009 | De Lega et al. | |
| 7,633,627 | B2 | 12/2009 | Choma et al. | |
| 7,636,168 | B2 | 12/2009 | De Lega et al. | |
| 7,761,139 | B2 | 7/2010 | Tearney et al. | |
| 2002/0143243 | A1 | 10/2002 | Georgakoudi et al. | |
| 2002/0171831 | A1 | 11/2002 | Backman et al. | |
| 2003/0042438 | A1 | 3/2003 | Lawandy et al. | |
| 2003/0137669 | A1 | 7/2003 | Rollins et al. | |
| 2004/0215296 | A1 | 10/2004 | Ganz et al. | |
| 2004/0223162 | A1 | 11/2004 | Wax | |
| 2005/0004453 | A1 | 1/2005 | Tearney et al. | |
| 2005/0053974 | A1 | 3/2005 | Lakowicz et al. | |
| 2006/0132790 | A1 | 6/2006 | Gutin | |
| 2006/0158657 | A1 | 7/2006 | De Lega et al. | |
| 2006/0164643 | A1 | 7/2006 | Giakos | |
| 2006/0256343 | A1 | 11/2006 | Choma et al. | |
| 2006/0285635 | A1 | 12/2006 | Boppart et al. | |
| 2007/0002327 | A1 | 1/2007 | Zhou et al. | |
| 2007/0015969 | A1 | 1/2007 | Feldman et al. | |
| 2007/0027391 | A1 | 2/2007 | Kohno | |
| 2007/0086013 | A1 | 4/2007 | De Lega et al. | |
| 2007/0133002 | A1 | 6/2007 | Wax et al. | |
| 2007/0165234 | A1 | 7/2007 | Podoleanu | |
| 2007/0201033 | A1 | 8/2007 | Desjardins et al. | |
| 2008/0037024 | A1 | 2/2008 | Backman et al. | |
| 2008/0058629 | A1 | 3/2008 | Seibel et al. | |
| 2008/0249369 | A1 | 10/2008 | Seibel et al. | |
| 2008/0255461 | A1 | 10/2008 | Weersink et al. | |
| 2009/0009759 | A1 | 1/2009 | Backman et al. | |
| 2009/0075391 | A1 | 3/2009 | Fulghum, Jr. | |

FOREIGN PATENT DOCUMENTS

| | | | |
|---|---|---|---|
| EP | 0243005 | A2 | 10/1987 |
| EP | 1021126 | B1 | 7/2004 |
| WO | 99/18845 | A1 | 4/1999 |
| WO | 00/42912 | A1 | 7/2000 |
| WO | 2007/133684 | A2 | 11/2007 |

OTHER PUBLICATIONS

Xie, Tuqiang et al., "Fiber-Optic-Bundle-Based Optical Coherehence Tomography," Optic Letters, vol. 30, No. 14, Jul. 15, 2005.

Pyhtila, John W. et al., "Fourier-Domain Angle-Resolved Low Coherence Interferometry Through an Endoscopic Fiber Bundle for Light-Scattering Spectroscopy," Optic Letters, vol. 31, No. 6, Mar. 15, 2006.

Hausler, G. et al., "Coherence Radar and Spectral Radar—New Tools for Dermatological Diagnosis," Journal of Biomedical Optics, vol. 3, Jan. 1998.

Pyhtila, John W. et al., "Rapid, Depth-Resolved Light Scattering Measurements using Fourier Domain, Angle-Resolved Low Coherence Interferometry," Optics Express, vol. 12, No. 25, Dec. 13, 2004.

(Continued)

*Primary Examiner* — Hwa S. A Lee
(74) *Attorney, Agent, or Firm* — Withrow & Terranova PLLC

(57) ABSTRACT

An apparatus and method for obtaining depth-resolved spectra for the purpose of determining the size of scatterers by measuring their elastic scattering properties. Depth resolution is achieved by using a white light source in a Michelson interferometer and dispersing a mixed signal and reference fields. The measured spectrum is Fourier transformed to obtain an axial spatial cross-correlation between the signal and reference fields with near 1 μm depth-resolution. The spectral dependence of scattering by the sample is determined by windowing the spectrum to measure the scattering amplitude as a function of wavenumber.

64 Claims, 10 Drawing Sheets

OTHER PUBLICATIONS

Pyhtila, John W. et al., "Determining Nuclear Morphology Using an Improved Angle-Resolved Low Coherence. Interferometry System," Optics Express, vol. 11, No. 25, Dec. 15, 2003.
Wax, Adam et al., "Cellular Organization and Substructure Measured Using Angle-Resolved Low-Coherence Interferometry," Biophysical Journal, Apr. 2002, pp. 2256-2264, vol. 82.
Wax, Adam et al., "Measurement of Angular Distributions by Use of Low-Coherence Interferometry for Light-Scattering Spectroscopy," Optics Letters, Mar. 15, 2001, pp. 322-324, vol. 26, No. 6.
Wax, Adam et al., "Determination of Particle Size Using the Angular Distribtion of Backscattered Light as Measured with Low-Coherence Interferometry," Journal of the Optical Society of America, Apr. 2002, pp. 737-744, vol. 19, No. 4.
Wax, Adam et al., "In Situ Detection of Neoplastic Transformation and Chemopreventive Effects in Rat Esophagus Epithelium Using Angle-Resolved Low-Coherence Interferometry," Cancer Research, Jul. 1, 2003, pp. 3556-3559, vol. 63, No. 13.
Leitgeb, R. et al., "Performance of Fourier Domain vs. Time Domain Optical Coherence Tomography," Optics Express, vol. 11, No. 8, Apr. 21, 2003, pp. 889-894.
de Boer, Johannes F. et al., "Improved Signal-To-Noise Ratio in Spectral-Domain Compared with Time-Domain Optical Coherence Tomography," Optics Letters, vol. 28, No. 21, Nov. 1, 2003, pp. 2067-2069, http://oa.osa.org/abstract.cfm?id=86605.
Choma, Michael A. et al., "Sensitivity Advantage of Swept Source and Fourier Domain Optical Coherence Tomography," Optics Express, vol. 11, No. 18, Sep. 8, 2003, pp. 2183-2189.
Kim, Y.L. et al., "Simultaneous Measurement of Angular and Spectral Properties of Light Scattering for Characterization of Tissue Microarchitecture and its Alteration in Early Precancer," IEEE Journal of Selected Topics in Quantum Electronics, vol. 9, Issue 2, Mar./Apr. 2003, pp. 243-256, http://ieeexploreieee_org/xpl/freeabs_all.jsp?tp=&arnumber=1238988&isnumber=27791.
Roy, Hemant K. et al., "Four-Dimensional Elastic Light-Scattering Fingerprints as Preneoplastic Markers in the Rat Model of Colon Carcinogenesis," Gastroenterology, vol. 126, Issue 4, Apr. 2004, pp. 1071-1081, http://www.gastrojoumal.org/article/PIIS0016508501000290/abstract.
Wax, Adam et al., "Prospective Grading of Neoplastic Change in Rat Esophagus Epithelium Using Angle-Resolved Low-Coherence Interferometry," Journal of Biomedical Optics, vol. 10(5), Sep./Oct. 2005, pp. 051604-1 through 051604-10.
Brown, William J. et al., "Review and Recent Development of Angle-Resolved Low-Coherence Interferometry for Detection of Precancerous Cells in Human Esophageal Epithelium," IEEE Journal of Selected Topics in Quantum Electronics, vol. 14, No. 1, Jan./Feb. 2008, pp. 88-97.
Wax, Adam et al., "Fourier-Domain Low-Coherence Interferometry for Light-Scaterring Spectroscopy," Optic Letters, vol. 28, No. 14, Jul. 15, 2003, pp. 1230-1232.
Backman, V. et al., "Measuring Cellular Structure at Submicrometer Scale with Light Scattering Spectroscopy," IEEE J. Sel. Top. Quantum Electron, vol. 7, Issue 6, Nov./Dec. 2001, pp. 887-893.
Backman, V. et al., "Detection of Preinvasive Cancer Cells," Nature 406, Jul. 6, 2000, pp. 35-36.
Wojtkowski, M. et al., "Full Range Complex Spectral Optical Coherence Tomography Technique in Eye Imaging ," Optics Letters, vol. 27, Issue 16, Aug. 15, 2002, pp. 1415-1417.
Wojtkowski, M. et al., "In Vivo Human Retinal Imaging by Fourier Domain Optical Coherence Tomography," J. Biomed. Opt., vol. 7, No. 3, Jul. 1, 2002, pp. 457-463.
Leitgeb, R. et al., "Spectral Measurement of Absorption by Spectroscopic Frequency-Domain Optical Coherence Tomography," Optic Letters, vol. 25, Issue 11, Jun. 1, 2000, pp. 820-822.
Morgner, U. et al., "Spectroscopic Optical Coherence Tomography," Optic Letters, vol. 25, Issue 2, Jan. 15, 2000, pp. 111-113.
Tuchin, V. et al., Tissue Optics: Light Scattering Methods and Instruments for Medical Diagnosis, SPIE, May 2000.
Amoozegar, Cyrus et a., "Experimental Verification of T-matrix-based Inverse Light Scattering Analysis for Assessing Structure of Spheroids as Models of Cell Nuclei," Applied Optics, vol. 48, No. 10, to be published Apr. 1, 2009, 7 pages.
Graf, R. N. et al., "Parallel Frequency-Domain Optical Coherence Tomography Scatter-Mode Imaging of the Hamster Cheek Pouch Using a Thermal Light Source," Optics Letters, vol. 33, No. 12, Jun. 15, 2008, pp. 1285-1287.
Robles, Francisco et al., "Dual Window Method for Processing Spectroscopic OCT Signals with Simultaneous High Spectral and Temporal Resolution," Optical Society of America, 2008, 12 pages.
Keener, Justin D. et al., "Application of Mie Theory to Determine the Structure of Spheroidal Scatterers in Biological Materials," Optics Letters, vol. 32, No. 10, May 15, 2007, pp. 1326-1328.
Chalut, Kevin J. et al., "Application of Mie Theory to Assess Structure of Spheroidal Scattering in Backscattering Geometries," J. Opt. Soc. Am. A, vol. 25, No. 8, Aug. 2008, pp. 1866-1874.
Chalut, Kevin J., et al., "Label-Free, High-Throughput Measurements of Dynamic Changes in Cell Nuclei Using Angle-Resolved Low Coherence Interferometry," Biophysical Journal, vol. 94, Jun. 2008, pp. 4948-4956.
Giacomelli, Michael G. et al., "Application of the T-matrix Method to Determine the Structure of Spheroidal Cell Nuclei with Angle-resolved Light Scattering," Optics Letters, vol. 33, No. 21, Nov. 1, 2008, pp. 2452-2454.
Wax, Adam, "Studying the Living Cell Using Light Scattering and Low-Coherence Interferometry," Laser Biomedical Research Center, MIT Spectroscopy Laboratory, presented at Case Western Reserve University 2002, Feb. 1, 2002.
Pyhtila, John W. et al., "Polarization Effects on Scatterer Sizing Accuracy Analyzed with Frequency-Domain Angle-Resolved Low-Coherence Interferometry," Applied Optics, vol. 46, No. 10, Apr. 1, 2007.
Pyhtila, John W. et al., "Coherent Light Scattering by In Vitro Cell Arrays Observed with Angle-Resolved Low Coherence Interferometry," SPIE, vol. 5690, 2005.
Wax, Adam et al., "Angular Light Scattering Studies Using Low-Coherence Interferometry," SPIE, vol. 4251, 2001.

* cited by examiner

FOURIER DOMAIN LOW-COHERENCE INTERFEROMETRY FOR LIGHT SCATTERING SPECTROSCOPY APPARATUS AND METHOD

Matter enclosed in heavy brackets [ ] appears in the original patent but forms no part of this reissue specification; matter printed in italics indicates the additions made by reissue.

BACKGROUND OF THE INVENTION

1. Field of the Invention

The present invention relates to an apparatus and method for obtaining depth-resolved spectra for the purpose of determining structure by measuring elastic scattering properties. More particularly, Fourier domain, low-coherence interferometry techniques are applied to light scattering spectroscopy. This approach permits the viewing and recovery of depth-resolved structures, as well as obtaining spectroscopic information about scattered light as a function of depth.

2. Background of the Related Art

Accurately measuring small objects or other physical phenomena is a goal that is pursued in many diverse fields of scientific endeavor. For example, in the study of cellular biology and cellular structures, light scattering spectroscopy (LSS) has received much attention recently as a means for probing cellular morphology and the diagnosing of dysplasia. The disclosures of the following references are incorporated by reference in their entirety:

Backman, V., V. Gopal, M. Kalashnikov, K. Badizadegan, R. Gurjar, A. Wax, I. Georgakoudi, M. Mueller, C. W. Boone, R. R. Dasari, and M. S. Feld, IEEE J. Sel. Top. Quantum Electron., 7(6): p. 887-893 (2001); Mourant, J. R., M. Canpolat, C. Brocker, O. Esponda-Ramos, T. M. Johnson, A. Matanock, K. Stetter, and J. P. Freyer, J. Biomed. Opt., 5(2): p. 131-137 (2000); Wax, A., C. Yang, V. Backman, K. Badizadegan, C. W. Boone, R. R. Dasari, and M. S. Feld, Biophysical Journal, 82: p. 2256-2264 (2002); Georgakoudi, I., E. E. Sheets, M. G. Müller, V. Backman, C. P. Crum, K. Badizadegan, R. R. Dasari, and M. S. Feld, Am J Obstet Gynecol, 186: p. 374-382 (2002); Backman, V., M. B. Wallace, L. T. Perelman, J. T. Arendt, R. Gurjar, M. G. Muller, Q. Zhang, G. Zonios, E. Kline, T. McGillican, S. Shapshay, T. Valdez, K. Badizadegan, J. M. Crawford, M. Fitzmaurice, S. Kabani, H. S. Levin, M. Seiler, R. R. Dasari, I. Itzkan, J. Van Dam, and M. S. Feld, Nature, 406(6791): p. 35-36 (2000); Wax, A., C. Yang, M. Mueller, R. Nines, C. W. Boone, V. E. Steele, G. D. Stoner, R. R. Dasari, and M. S. Feld, Cancer Res, (accepted for publication).

The LSS technique examines variations in the elastic scattering properties of cell organelles to infer their sizes and other dimensional information. In order to measure cellular features in tissues and other cellular structures, it is necessary to distinguish the singly scattered light from diffuse light, which has been multiply scattered and no longer carries easily accessible information about the scattering objects. This distinction or differentiation can be accomplished in several ways, such as the application of a polarization grating, by restricting or limiting studies and analysis to weakly scattering samples, or by using modeling to remove the diffuse component (s).

As an alternative approach for selectively detecting singly scattered light from sub-surface sites, low-coherence interferometry (LCI) has also been explored as a method of LSS.

Experimental results have shown that using a broadband light source and its second harmonic allows the recovery of information about elastic scattering using LCI [7].

More recently, angle-resolved LCI (a/LCI) has demonstrated the capability of obtaining structural information by examining the angular distribution of scattered light from the sample or object under examination. The a/LCI technique has been successfully applied to measuring cellular morphology and to diagnosing intraepithelial neoplasia in an animal model of carcinogenesis.

The above references are incorporated by reference herein where appropriate for appropriate teachings of additional or alternative details, features and/or technical background.

SUMMARY OF THE INVENTION

The claimed exemplary embodiments of the present invention address some of the issues presented above.

An object of the invention is to solve at least the above problems and/or disadvantages and to provide at least the advantages described hereinafter.

In one exemplary embodiment of the present invention, an apparatus comprises a first receiver that receives a first reference light and outputs a second reference light. A second receiver that receives a first sample light and outputs a second sample light and wherein the second sample light contains light scattered from a sample when at least a portion of the first sample light is scattered from a sample. A cross-correlator that receives and cross-correlates the second reference light with the second sample light. The cross-correlator may be a spatial cross-correlator.

In another exemplary embodiment of the present invention, a reference arm receives a first reference light and outputs a second reference light. A sample receives a first sample light and outputs a second sample light and wherein the second sample light contains light scattered from the sample when at least a portion of said first sample light is scattered from the sample. A spatial cross-correlator receives and cross correlates the second reference light with the second sample light. The spatial cross-correlator comprises a detector and a processing unit. The detector outputs an interference term to the processing unit. The processing unit processes the interference term to yield depth resolved cross-correlation reflection profiles of the sample. The processing unit first applies a Gaussian window and then a Fourier transform transforms the interference term to yield depth resolved cross-correlation reflection profiles of the sample. The Fourier transform obtains an axial spatial cross-correlation between a signal field(s) and a reference field(s). A light source outputs light, which contains the first sample light and the first reference light.

In another exemplary embodiment of the present invention, a method comprises receiving a first reference light and outputting a second reference light. A first sample light is received and a second sample light is output. The second sample light contains light scattered from a sample when at least a portion of the first sample light is scattered from a sample along with the reception and cross correlation of the second reference light with the second sample light.

In another exemplary embodiment, a method comprises receiving light and splitting at least a portion of the light into reference light and sample light. At least a portion of said reference light is reflected from a reference surface to yield reflected reference light. At least a portion of the sample light is scattered from a sample to yield scattered sample light, and the scattered sample and the reflected reference light are mixed. Information is recovered about the scattered sample light. The mixing comprises detecting an intensity of the scattered sample light and the reflected reference light. Recovering information comprises extracting an interference term from a total intensity. Recovering information can further comprise applying a mathematical operator to the interference term to recover the spectral information about the scattered sample light at a particular depth to yield depth resolved cross-correlation reflection points of the sample. The mathematical operator used is preferably a Gaussian window.

BRIEF DESCRIPTION OF THE DRAWINGS

The invention will be described in detail with reference to the following drawings in which like reference numerals refer to like elements wherein.

DETAILED DESCRIPTION OF PREFERRED EMBODIMENTS

Figure 1A:
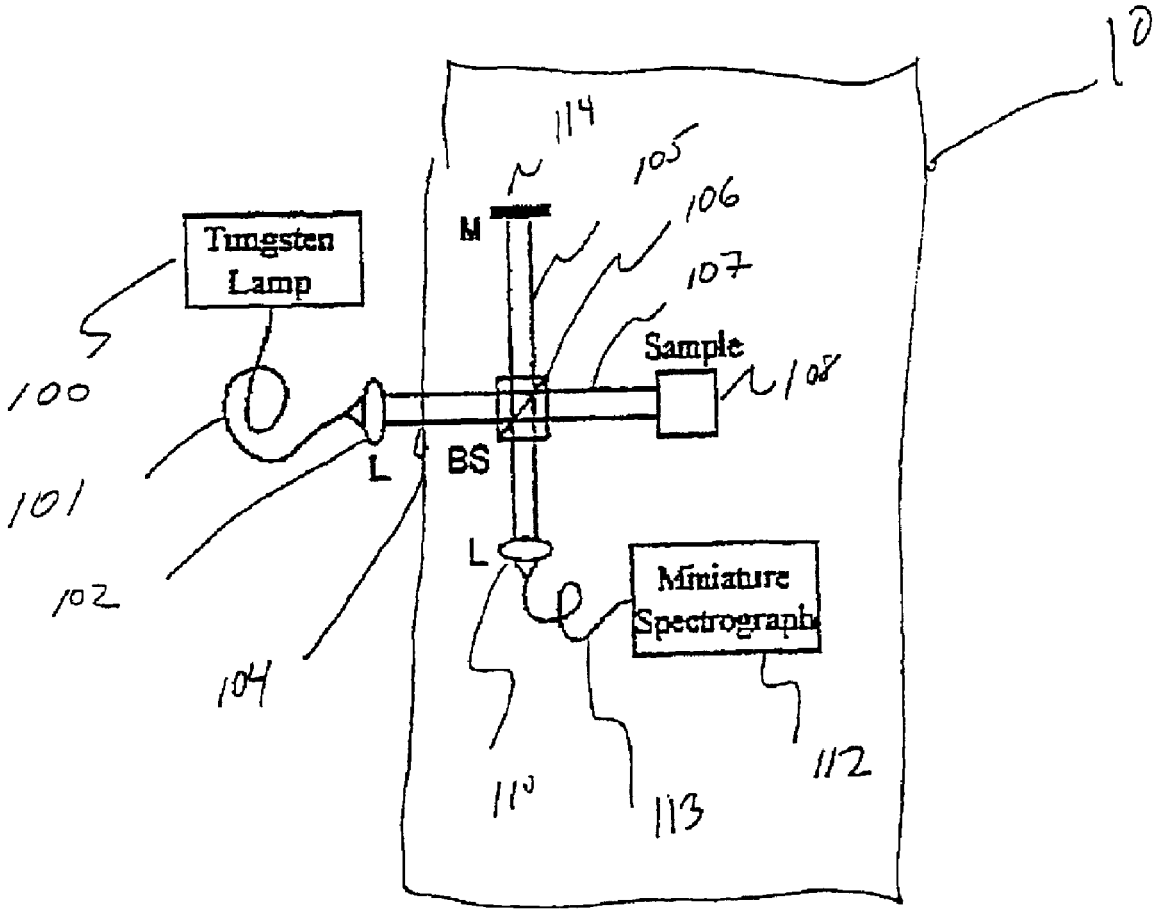
FIG. 1A is a diagram of an exemplary embodiment of an fLCI system.

In the following detailed description of the various exemplary embodiments, reference is made to the accompanying drawings that show, by way of illustration, specific embodiments in which the invention may be practiced. In the drawings, like numerals describe substantially similar components throughout the several views. These embodiments are described in sufficient detail to enable those skilled in the art to practice the invention. Other embodiments may be utilized without departing from the scope of the present invention. Moreover, it is to be understood that various embodiments of the invention, although different, are not necessarily mutually exclusive. For example, a particular feature, structure, or characteristic described in one embodiment may be included within other embodiments. Therefore, the following detailed description is not to be taken in a limiting sense. The scope of the present invention is delineated by the claims, along with the full scope of equivalents to which such claims are entitled.

The contents of the following references are incorporated by reference in their entirety: Wojtkowski, M., A. Kowalczyk, R. Leitgeb, and A. F. Fercher, Opt. Lett., 27(16): p. 1415-1417 (2002); Wojtkowski, M., R. Leitgeb, A. Kowalczyk, T. Bajraszewski, and A. F. Fercher, J. Biomed. Opt., 7(3): p. 457-463 (2002); Leitgeb, R., M. Wojtkowski, A. Kowalczyk, C. K. Hitzenberger, M. Sticker, and A. F. Fercher, Opt. Lett., 25(11): p. 820-822 (2000).

In general, spectral radar makes use of techniques where depth-resolved structural information is recovered by applying a Fourier transform to the spectrum of two mixed fields. In fLCI, the aforementioned approach used in spectral radar applications is extended to recover not only depth-resolved structure, but also to obtain spectroscopic information about scattered light as a function of depth. The capabilities of fLCI enable extracting the size of polystyrene beads in a sub-surface layer based on their light scattering spectrum. The apparatus and method according to exemplary embodiments of the invention can be applied to many different areas. One such area of application is to recover nuclear morphology of sub-surface cell layers.

One exemplary embodiment of the fLCI scheme is shown in FIG. 1A. White light from a Tungsten light source 100 (e.g. 6.5 W, Ocean Optics™) is coupled into a multimode fiber 101 (e.g. 200 μm core diameter). The output of the fiber 101 is collimated by an achromatic lens 102 to produce a beam 104 (e.g. a pencil beam 5 mm in diameter). The beam 104 is then forwarded to an fLCI system 10.

This illumination scheme achieves Kohler illumination in that the fiber acts as a field stop, resulting in the proper alignment of incident or illuminating light and thereby achieving critical illumination of the sample. In the fLCI system 10, the white light beam is split by the beamsplitter 106 (BS) into a reference beam 105 and an input beam 107 to the sample 108. The light scattered by the sample 108 is recombined at the BS 106 with light reflected by the reference mirror 114 (M).

The reference beam 105 in conjunction with the reference mirror 114 forms a portion of a reference arm that receives a first reference light and outputs a second reference light. The input beam 107 and the sample 108 form a portion of a sample arm that receives a first sample light and outputs a second sample light.

Those skilled in the art will appreciate that the light beam can be split into a plurality of reference beams and input beams (e.g. N reference beams and N input beams) without departing from the spirit and scope of the present invention. Further, the splitting of the beams may be accomplished with a beamsplitter or a fiber splitter in the case of an optical fiber implementation of and exemplary embodiment of the present invention.

In the exemplary embodiment of the present invention shown in FIG. 1A, the combined beam is coupled into a multimode fiber 113 by an aspheric lens 110. Again, other coupling mechanisms or lens types and configurations may be used without departing from the spirit and scope of the present invention. The output of the fiber coincides with the input slit of a miniature spectrograph 112 (e.g. USB2000, Ocean Optics™), where the light is spectrally dispersed and detected.

The detected signal is linearly related to the intensity as a function of wavelength $I(\lambda)$, which can be related to the signal and reference fields ($E_s$, $E_r$) as:

$$\langle I(\lambda)\rangle = \langle |E_s(\lambda)|^2\rangle + \langle |E_r(\lambda)|^2\rangle + 2\mathrm{Re}\langle E_s(\lambda)E^*_r(\lambda)\rangle \cos\phi \quad (1)$$

where $\phi$ is the phase difference between the two fields and <. . .> denotes an ensemble average.

The interference term is extracted by measuring the intensity of the signal and reference beams independently and subtracting them from the total intensity.

The axial spatial cross-correlation function, $\Gamma_{SR}(z)$ between the sample and reference fields is obtained by resealing the wavelength spectrum into a wavenumber ($k=2\pi/\lambda$) spectrum then Fourier transforming:

$$\Gamma_{SR}(z)=\int dk e^{ikz}<E_s(k)E^*_r(k)>\cos\phi. \quad (2)$$

This term is labeled as an axial spatial cross-correlation as it is related to the temporal or longitudinal coherence of the two fields.

Figure 1B:
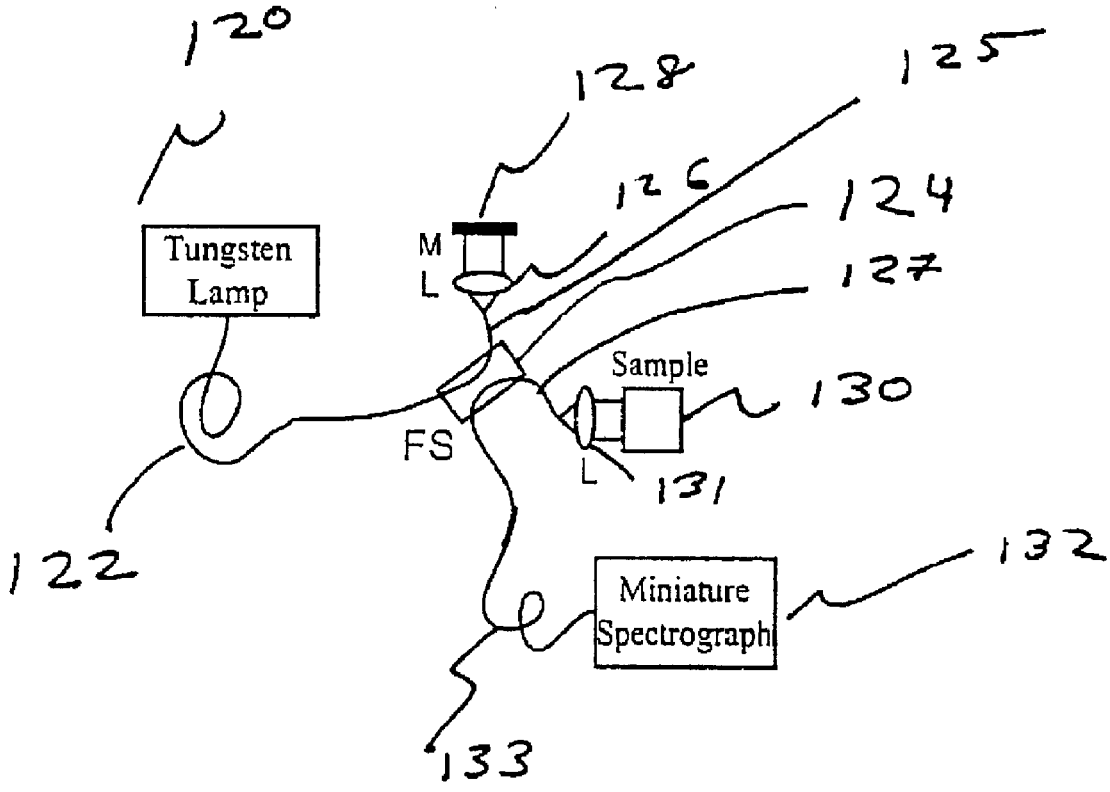
FIG. 1B is a diagram of another exemplary embodiment of an fLCI system using fiber optic coupling.

Another exemplary embodiment of an fLCI scheme is shown in FIG. 1B. In this exemplary embodiment, fiber optic cable is used to connect the various components. Those skilled in the art will appreciate that other optical coupling mechanisms, or combinations thereof, may be used to connect the components without departing from the spirit and scope of the present invention.

In FIG. 1B, white light from a Tungsten light source 120 is coupled into a multimode fiber 122 and the white light beam in the multimode fiber is split by the fiber splitter (FS) 124 into a reference fiber 125 and an sample fiber 127 to the sample 130. The fiber splitter 124 is used to split light from one optical fiber source into multiple sources.

The reference light in reference fiber 125, in conjunction with a lens 126 (preferably an aspheric lens) and the reference mirror 128, forms a portion of a reference arm that receives a first reference light and outputs a second reference light. Specifically, reference light in reference fiber 125 is directed to the reference mirror 128 by lens 126, and the reference light reflected by the reference mirror 128 (second reference light) is coupled back into the reference fiber 125 with lens 126. The sample light in sample fiber 127 and the sample 130 form a portion of a sample arm that receives a first sample light and outputs a second sample light. Specifically, sample light in sample fiber 127 is directed to the sample 130 by lens 131 (preferably as aspheric lens), and at least a portion of the sample light scattered by the sample 130 is coupled into the sample fiber 127 by lens 131. In the exemplary embodiment shown in FIG. 1B, the sample 130 is preferably spaced from lens 131 by a distance approximately equal to the focal length of lens 131.

At least a portion of the reflected reference light in reference fiber 125 and at least a portion of the scattered sample light on sample fiber 127 are coupled into a detector fiber 133 by the FS 124.

The output of detector fiber 133 coincides with the input of a miniature spectrograph 132, where the light is spectrally dispersed and detected.

Figure 2:
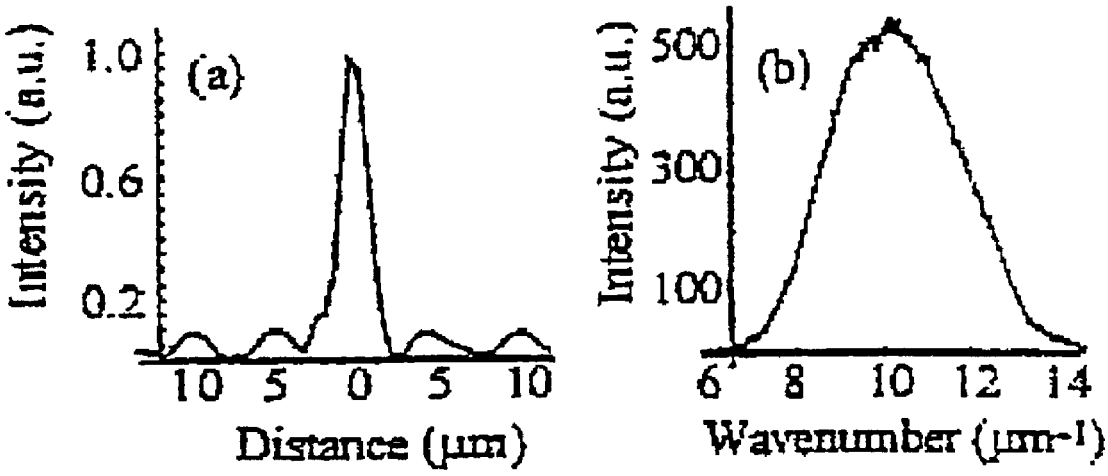
FIG. 2 is a diagram illustrating exemplary properties of a white light source.

FIG. 2 illustrates some of the properties of a white light source. FIG. 2(a) illustrates an autocorrelation function showing a coherence length ($l_C$=1.2 μm). FIG. 2(a) shows the cross-correlation between the signal and reference fields when the sample is a mirror, and this mirror is identical to the reference mirror (M). In this exemplary scenario, the fields are identical and the autocorrelation is given by the transform of the incident field spectrum, modeled as a Gaussian spectrum with center wavenumber $k_o$=10.3 $\mu m^{-1}$ and l/e width $\Delta k_{l/e}$=2.04 $\mu m^{-1}$ (FIG. 2(b)).

FIG. 2(b) shows an exemplary spectrum of light source that can be used in accordance with the present invention.

From this autocorrelation, the coherence length of the field, $l_c$=1.21 μm is determined. This is slightly larger than the calculated width of $l_c=2/\Delta k_{l/e}$=0.98 μm, with any discrepancy most likely attributed to uncompensated dispersion effects. Note that rescaling the field into wavenumber space is a nonlinear process which can skew the spectrum if not properly executed [13].

In data processing, a fitting algorithm is applied (e.g. a cubic spline fit) to the rescaled wavenumber spectrum and then resampled (e.g. resample with even spacing). The resampled spectrum is then Fourier transformed to yield the spatial correlation of the sample. Those skilled in the art will appreciate that other frequency based algorithms or combinations of algorithms can be used in place of the Fourier transform to yield spatial correlation. One example of a software tool that can be used to accomplish this processing in real time or near real time is to use LabView™ software.

In one exemplary embodiment of the present invention, the sample consists of a glass coverslip (e.g., thickness, d~200 μm) with polystyrene beads which have been dried from suspension onto the back surface (1.55 μm mean diameter, 3% variance). Thus, the field scattered by the sample can be expressed as:

$$E_s(k)=E_{front}(k)e^{ik\delta_z}+E_{back}(k)e^{ik(\delta_{z+nd})} \quad (3)$$

In equation 3, $E_{front}$ and $E_{back}$ denote the field scattered by the front and back surfaces of the coverslip, and δz is the difference between the path length of the reference beam and that of the light reflected from the front surface and n the index of refraction of the glass. The effect of the microspheres will appear in the $E_{back}$ term as the beads are small and attached closely to the back surface. Upon substituting equation 3 into equation 2, a two peak distribution with the width of the peaks given by the coherence length of the source is obtained.

In order to obtain spectroscopic information, a Gaussian window is applied to the interference term before performing the Fourier transform operation. Those skilled in the art will appreciate that other probabilistic windowing methodologies may be applied without departing from the spirit and scope of the invention. This makes it possible to recover spectral information about light scattered at a particular depth.

The windowed interference term takes the form:

$$<E_s(k)E^*_r(k)>\exp[-((k-k_w)/\Delta k_w)^2]. \quad (4)$$

The proper sizing of a windowed interference term can facilitate the processing operation. For example, by selecting a relatively narrow window ($\Delta k_w$ small) compared to the features of $E_s$ and $E_k$, we effectively obtain <Es(kw)E* r(kw) >. In processing the data below, we use $\Delta k_w$=0.12 $\mu m^{-1}$ which degrades the coherence length by a factor of 16.7. This exemplary window setting enables the scattering at 50 different wavenumbers over the 6 $\mu m^{-1}$ span of usable spectrum.

Figure 3:
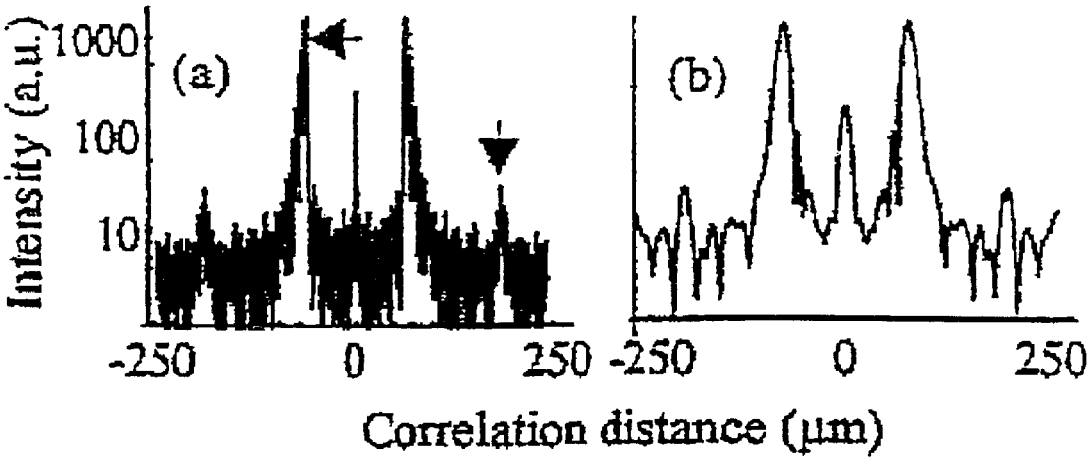
FIG. 3 is a diagram of an exemplary axial spatial cross-correlation function for a coverslip sample.

In FIG. 3, an axial spatial cross-correlation function for a coverslip sample is showed according to one embodiment of the invention. FIGS. 3(a) and (b) shows the depth resolved cross-correlation reflection profiles of the coverslip sample before and after the processing operations. In FIG. 3(a), a high resolution scan with arrows indicating a peak corresponding to each glass surface is shown. In FIG. 3(b), a low resolution scan is obtained from the scan in FIG. 3(a) is shown by using a Gaussian window.

Note that the correlation function is symmetric about z=0, resulting in a superposed mirror image of the scan. Since these are represented as cross-correlation functions, the plots are symmetric about z=0. Thus the front surface reflection for z>0 is paired with the back surface reflection for z<0, and vice versa.

In FIG. 3(a), the reflection from the coverslip introduces dispersion relative to the reflection from the reference arm, generating multiple peaks in the reflection profile. When the spectroscopic window is applied, only a single peak is seen for each surface, however several dropouts appear due to aliasing of the signal.

To obtain the spectrum of the scattered light, we repeatedly apply the Gaussian window and increase the center wavenumber by 0.12 $\mu m^{-1}$ between successive applications. As mentioned above, $\Delta k_w$=0.12 $\mu m^{-1}$ is used to degrade the coherence length by a factor of 16.7. This results in the generation of a spectroscopic depth-resolved reflection profile.

FIGS. 4(a) and (b) show the spectrum obtained for light scattered from the front (a) and back (b) surfaces of a coverglass sample respectively, when no microspheres are present. The reflection from the front surface appears as a slightly modulated version of the source spectrum. The spectrum of the reflection from the rear surface however has been significantly modified. Thus in equation 3, we now take $E_{front}(k)=E_s(k)$ and $E_{back}(k)=T(k)E_s(k)$, where T(k) represents the transmission through the coverslip.

Figure 5:
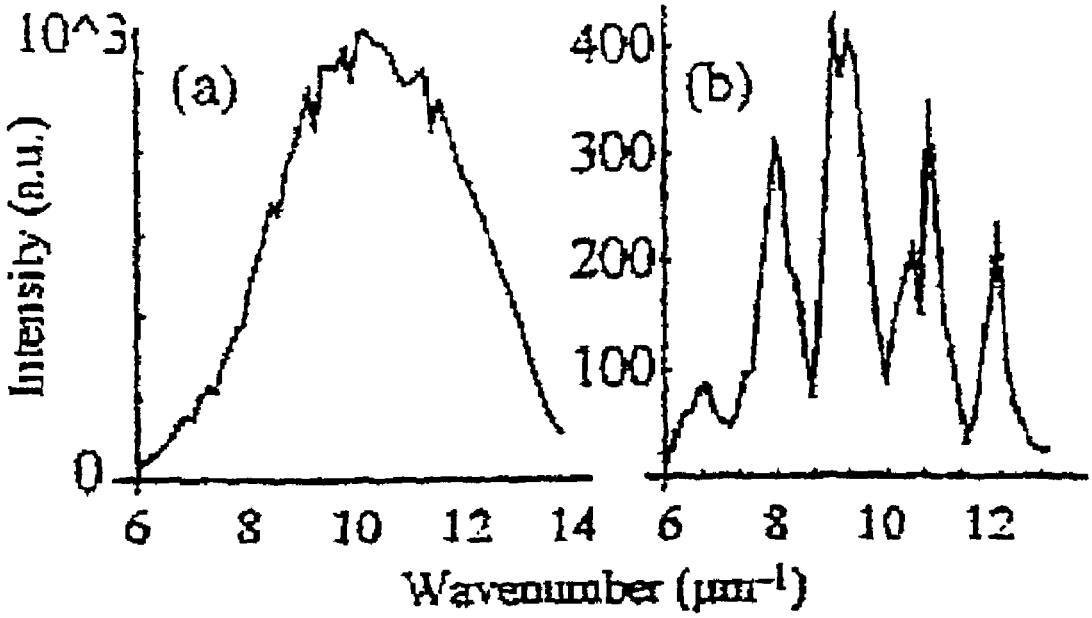
FIG. 5 is a diagram of exemplary spectra obtained for front and back surfaces of a coverglass sample when microspheres are present.

In FIG. 5, the spectra for light scattering obtained for front (a) and back (b) surfaces of a coverglass sample when microspheres are present on the back surface of the coverslip are shown in FIGS. 5(a) and (b). It can be seen that the reflected spectrum from the front surface has not changed significantly, as expected. However, the spectrum for the back surface is now modulated. We can examine the scattering properties S(k) of the microspheres by writing the scattered field as $E_{spheres}(k)=S(k)T(k)E_s(k)$ and taking the ratio $E_{spheres}(k)/E_{back}(k)=S(k)$, which is shown as a solid line in FIG. 6(a). It can be seen from this ratio that the microspheres induce a periodic modulation of the spectrum.

Figure 4:
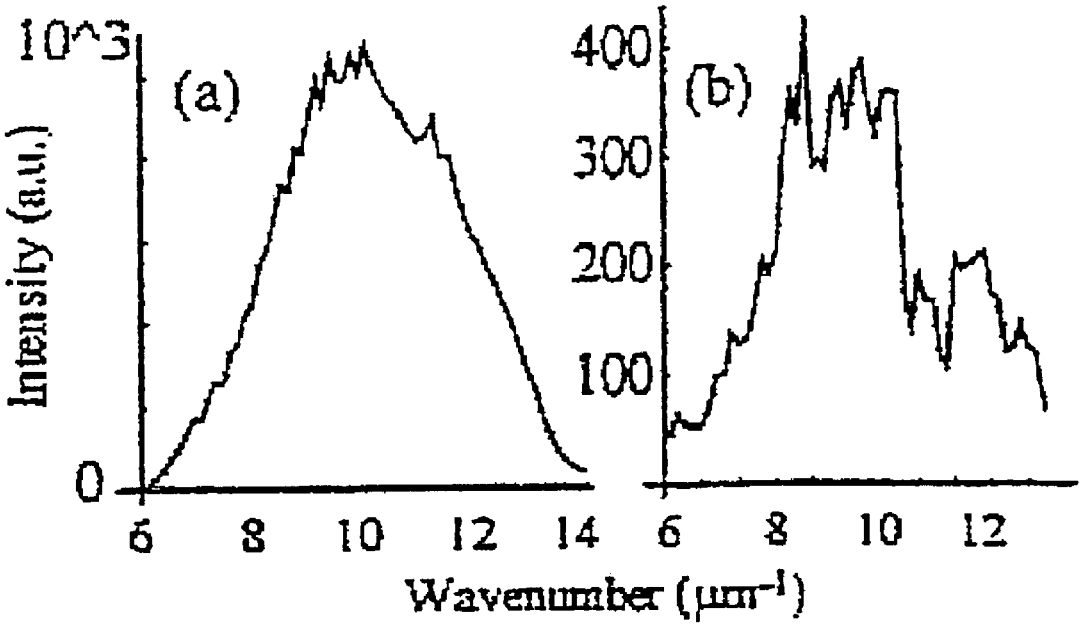
FIG. 4 is a diagram of exemplary spectra obtained for front and back surfaces of a coverglass sample when no microspheres are present.
Figure 6:
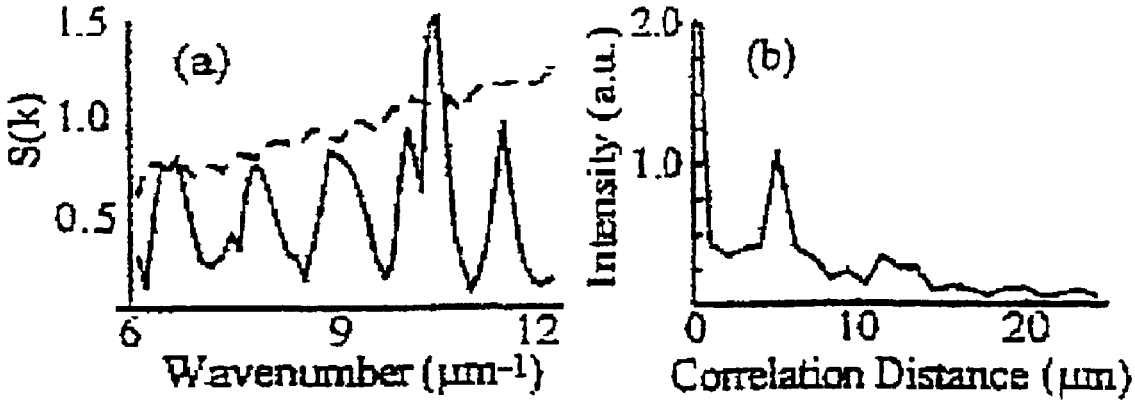
FIG. 6 is a diagram of exemplary ratios of spectra in FIGS. 4 and 5 illustrating scattering efficiency of spheres for front and back surface reflections.

In FIG. 6(a), a ratio of the spectra found in FIG. 4 and FIG. 5 is shown. This illustrates the scattering efficiency of spheres for front (represented by the dashed line) and back (represented by the solid line) surface reflections. In FIG. 6(b), a correlation function obtained from ratio of back surface reflections is shown. The peak occurs at the round trip optical path through individual microspheres, permitting the size of the spheres to be determined with sub-wavelength accuracy.

For comparison, the same ratio for the front surface reflections (dashed line in FIG. 6(a)) shows only a small linear variation. Taking the Fourier transform of S(k) yields a clear correlation peak (FIG. 6(b)), at a physical distance of z=5.24 μm. This can be related to the optical path length through the sphere by z=2nl with the index of the microspheres n=1.59. The diameter of the microspheres to be l=1.65 μm+/−0.33 μm, with the uncertainty given by the correlation pixel size. Thus with fLCI, we are able to determine the size of the microspheres with sub-wavelength accuracy, even exceeding the resolution achievable with this white light source and related art LCI imaging.

There are many applications of the various exemplary embodiments of the present invention. One exemplary application of fLCI is in determining the size of cell organelles, in particular the cell nucleus, in epithelial tissues. In biological media, for example, the relative refractive indices are lower for organelles compared to microspheres and thus, smaller scattering signals are expected. The use of a higher power light source will permit the smaller signals to be detected. Other examples include detection of sub-surface defects in manufactured parts, including fabricated integrated circuits, detection of airborne aerosols, such as nerve agents or biotoxins, and detection of exposure to such aerosols by examining epithelial tissues within the respiratory tract.

Additionally, the larger the size of the nucleus (compared to the microspheres in this experiment), the higher the frequency modulation of the spectrum. Those skilled in the art will appreciate that higher frequency oscillations are detected at a lower efficiency in Fourier transform spectroscopy techniques. Therefore, in order to detect these higher frequency oscillations, a higher resolution spectrograph is used.

Figure 7:
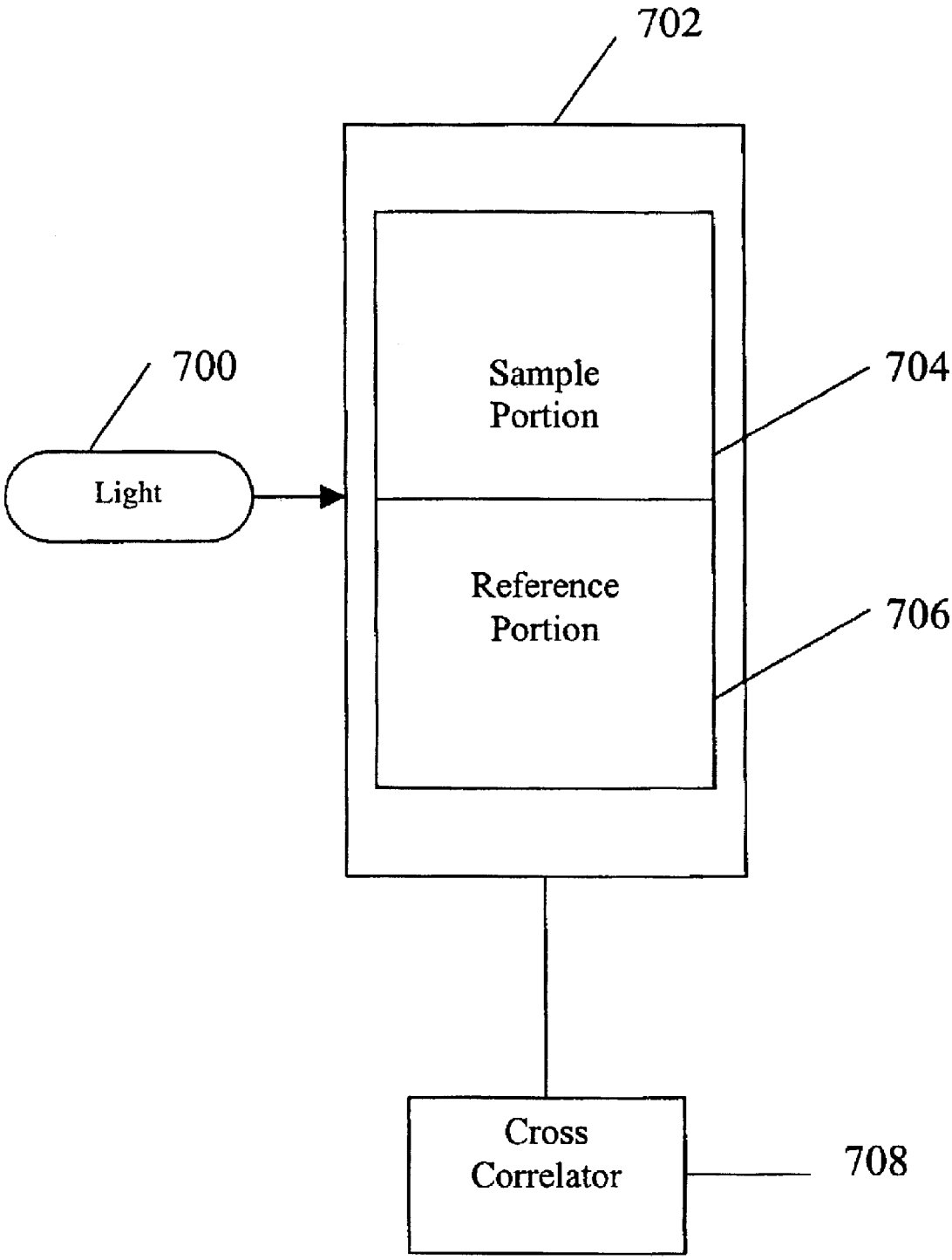
FIG. 7 is a diagram of a generalized version of the system shown in FIG. 1.

FIG. 7 illustrates a generalized embodiment of the fLCI system shown in FIG. 1 and discussed in greater detail above. In FIG. 7, a light source 700 (e.g. a multi-wavelength light) is coupled into an fLCI system 702. Within the fLCI system 702, a sample portion 704 and a reference portion 706 are located. The sample portion 704 includes a light beam and light scattered from a sample. For example, the sample portion 704 may include a sample holder, a free space optical arm, or an optical fiber. The reference portion 706 includes a light beam and light that is reflected from a reference. For example, the reference portion 706 may include an optical mirror. A cross-correlator 708 receives and cross-correlates light from the sample with light from the reference.

Figure 8:
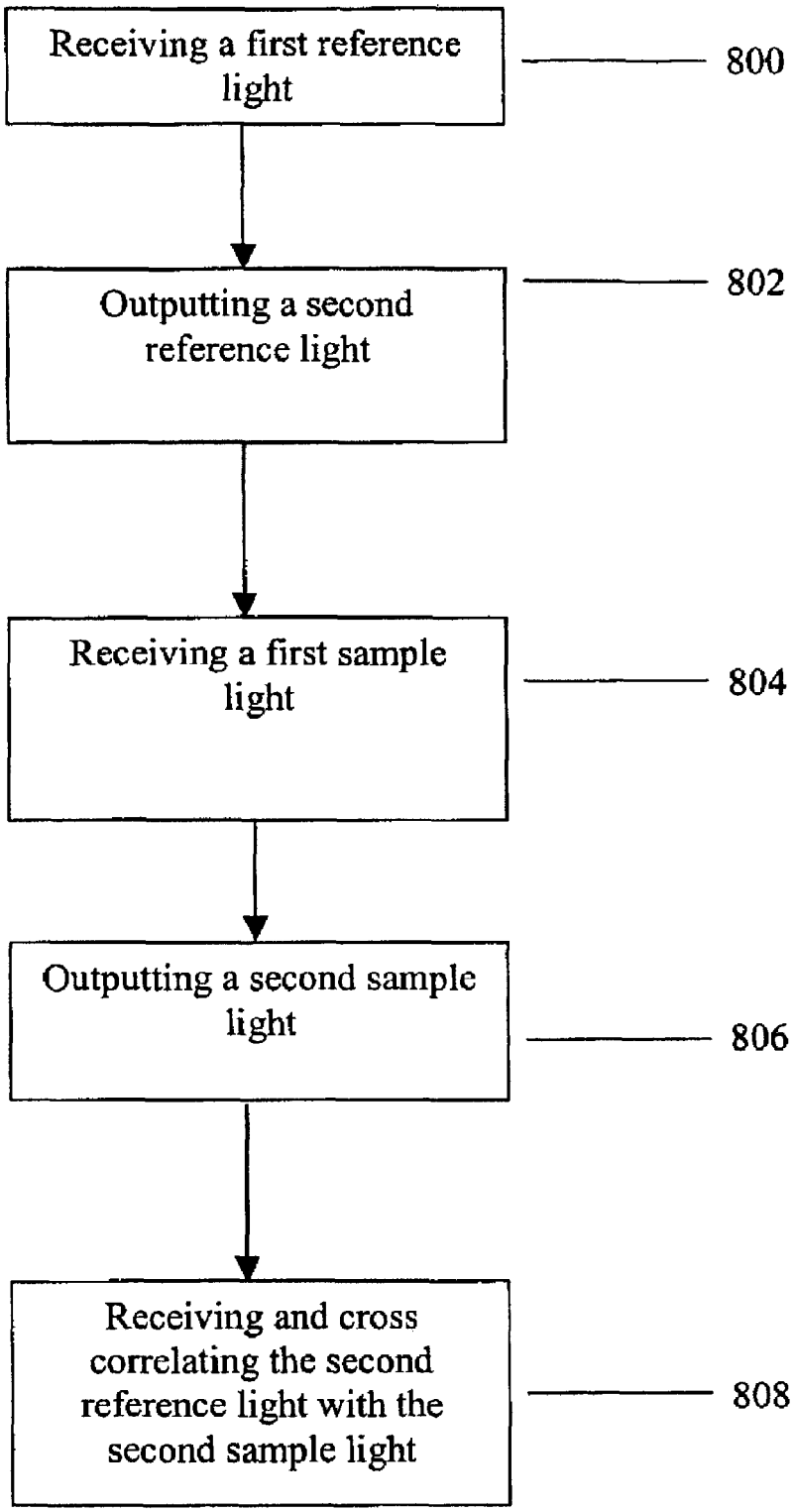
FIG. 8 is a block diagram of an exemplary embodiment of a method in accordance with the present invention.

FIG. 8 illustrates another exemplary embodiment of the present invention. In FIG. 8, a method is disclosed where a first reference light is received 800 and a second reference light is output 802. A first sample light is received 804 and a second sample light is output 806. The second sample light contains light scattered from a sample when at least a portion of the first sample light is scattered from a sample. The second reference light with the second sample light are received and cross-correlated 808.

Figure 9:
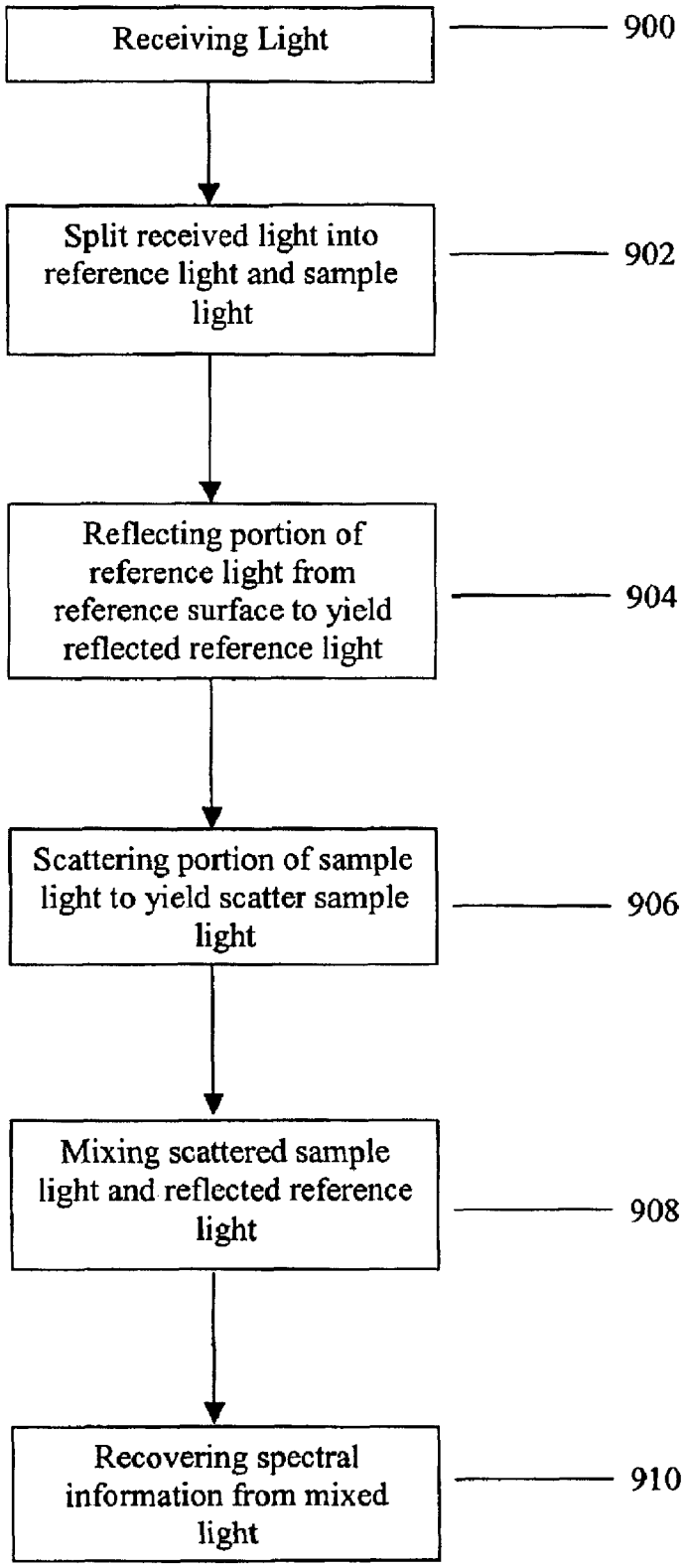
FIG. 9 is a block diagram of another exemplary embodiment of a method in accordance with the present invention.

FIG. 9 illustrates another exemplary embodiment of the present invention. In FIG. 9, a method is disclosed where light is received 900 from a sample that has been illuminated. At least a portion of the light is split into reference light and sample light 902. At least a portion of said reference light is reflected from a reference surface to yield reflected reference light 904. At least a portion of the sample light is scattered from a sample to yield scattered sample light 906. The scattered sample light and the reflected reference light are mixed 908. Spectral information is recovered about the scattered sample light 910.

The foregoing example illustrates how the exemplary embodiments of the present invention can be modified in various manners to improve performance in accordance with the spirit and scope of the present invention.

From the foregoing detailed description, it should be apparent that fLCI can recover structural information with sub-wavelength accuracy from sub-surface layers based on measuring elastic scattering properties. The simplicity of the system makes it an excellent candidate for probing cellular morphology in tissue samples and may one day serve as the basis for a biomedical diagnostic device.

The foregoing embodiments and advantages are merely exemplary and are not to be construed as limiting the present invention. The present teaching can be readily applied to other types of apparatuses. The description of the present invention is intended to be illustrative, and not to limit the scope of the claims. Many alternatives, modifications, and variations will be apparent to those skilled in the art. In the claims, means-plus-function clauses are intended to cover the structures described herein as performing the recited function and not only structural equivalents but also equivalent structures.

What is claimed is:

1. A method of obtaining depth-resolved spectra of a sample for determining size and depth characteristics of scatterers within the sample, comprising the steps of:

emitting a beam onto a splitter, wherein the splitter [is fixed with respect to the sample, and wherein the splitter] splits light from the [bean] *beam* to produce a reference beam, [which is reflected to produce a reflected reference beam,] and an input beam to the sample [comprised of a substrate having a first surface and a second surface];

cross-correlating the [reflected] reference beam with a [reflected] sample beam scattered from the sample as a result of the input beam by mixing the [reflected] reference beam and the [reflected] *scattered* sample beam;

spectrally dispersing the mixed [reflected] reference beam and the [reflected] *scattered* sample beam to yield a single [spectrally resolved,] *spectrally-resolved* cross-correlated reflection profile having depth-resolved information about the [reflected] *scattered* sample beam; and generating a spectroscopic depth-resolved reflection profile[, by processing] *that includes characteristics of scatterers within the sample by:*

*providing one or more spectral windows of* the single spectrally-resolved cross-correlated reflection profile [by: at a plurality of different center wavelengths, applying a window to the single spectrally-resolved cross-correlated reflection profile at] *, each of the one or more spectral windows having* a given center wavelength to obtain spectral information [at the given center wavelength] *about the sample for each of the one or more spectral windows*; and

[converting the windowed] *applying a Fourier transform to the* spectral information [via a Fourier transform] to recover depth-resolved information about the sample at [all] *each given* center [wavelengths] *wavelength* simultaneously.

2. The method of claim 1, further comprising recovering size information about the scatterers from the spectroscopic depth-resolved reflection profile.

3. The method of claim 2, wherein recovering the size information is obtained by measuring a frequency of a spectral modulation in the spectroscopic depth-resolved reflection profile.

4. The method of claim 2, wherein recovering the size information is obtained by comparing the spectroscopic depth-resolved reflection profile to a predicted analytical or numerical scattering distribution of the sample.

5. The method of claim 1, wherein [applying a processing algorithm] *providing one or more spectral windows* is comprised of [applying a] *providing one or more* Gaussian [window] *windows*, *one or more* multiple simultaneous windows, or *one or more* other window.

6. The method of claim 1, wherein the splitter is comprised from the group consisting of a beam splitter and an optical fiber splitter.

7. The method of claim 1, wherein emitting a beam onto the splitter comprises emitting a collimated beam.

8. The method of claim 7, wherein the input beam comprises a collimated beam.

9. The method of claim 7, wherein the [reflected] reference beam comprises a collimated beam.

10. The method of claim 1, wherein the beam is comprised of a light comprised of white light from an arc lamp or thermal source.

11. The method of claim 1, wherein cross-correlating the [reflected] reference beam with the [reflected] *scattered* sample beam comprises determining an interference term by measuring the intensity of the [reflected] *scattered* sample beam and the [reflected] reference beam independently and subtracting them from the total intensity of the [reflected] *scattered* sample beam.

12. The method of claim 1, wherein the [reflected] reference beam is [created by reflecting the reference beam] *reflected* off of a reference mirror.

13. The method of claim 1, wherein the length of the path of the reference beam is fixed.

14. The method of claim 1, wherein the splitter is attached to a fixed reference arm.

15. The method of claim 1, wherein the sample is attached to a fixed sample arm.

16. The method of claim 1, wherein dispersing the mixed reflected reference beam and [reflected] *scattered* sample beam is performed using a spectrograph.

17. A method of obtaining depth-resolved spectra of a sample comprised of a substrate having a first surface and a second surface for determining size and depth characteristics of scatterers within the sample, comprising the steps of:

emitting a beam onto a splitter [wherein the splitter is fixed with respect to the sample], wherein the splitter splits light from the beam to produce a [reference beam, which is reflected to produce a reflected] reference beam, and an input beam to the sample comprised of a substrate having a first surface and a second surface;

cross-correlating the [reflected] reference beam with a first [reflected] *scattered* sample beam comprised of a first portion of light scattered from the first surface, by mixing the [reflected] reference beam and the first portion of light;

cross-correlating the [reflected] reference beam with a second [reflected] *scattered* sample beam comprised of a second portion of light scattered from the second surface, by mixing the [reflected] reference beam and the second portion of light;

spectrally dispersing the mixed [reflected] reference beam and the first [reflected] *scattered* sample beam to yield a *first* single [first spectrally dispersed,] *spectrally-resolved* cross-correlated reflection profile having depth-resolved information about the first surface of the substrate;

spectrally dispersing the mixed [reflected] reference beam and the second [reflected] *scattered* sample beam to yield a *second* single [second spectrally dispersed,] *spectrally-resolved* cross-correlated reflection profile having depth-resolved information about the second surface of the substrate;

generating a first spectroscopic depth-resolved reflection profile [by processing the single spectrally dispersed, first cross-correlated reflection profile by:] *that includes characteristics of scatterers within the sample by:*

[at a plurality] *providing one or more first spectral windows* of [different center wavelengths, applying a window to] the *first* single [first spectrally dispersed,] *spectrally-resolved* cross-correlated reflection profile*, each of the one or more first spectral windows* at a given center wavelength to obtain [spectral information at the given center wavelength; and converting the windowed spectral information via a Fourier transform to recover depth-resolved] *first* spectral information about the first surface of the substrate [at all center wavelengths simultaneously] *for each of the one or more first spectral windows*; and

*applying a Fourier transform to the first spectral information to recover depth information about the first surface at each given center wavelength simultaneously; and* generating a second spectroscopic depth-resolved reflection profile [by processing the single] *that includes characteristics of scatterers within the sample by:*

*providing one or more* second [spectrally dispersed, cross-correlated reflection profile by: at a plurality of different center wavelengths, applying a window to the single] *spectral windows of the* first [spectrally dispersed,] *single spectrally-resolved* cross-correlated reflection profile*, each of the one or more second spectral windows* at a given center wavelength to obtain [spectral information at the given center wavelength; and]

[converting the windowed spectral information via a Fourier transform to recover depth-resolved] *second* spectral information about the second surface of the substrate [at all center wavelength simultaneously] *for each of the one or more second spectral windows; and*

*applying a Fourier transform to the second spectral information to recover depth information about the second surface at each given center wavelength simultaneously*.

18. The method of claim 17, wherein recovering size information about the sample is comprised of determining a ratio of the first spectroscopic depth-resolved reflection profile and the second spectroscopic depth-resolved reflection profile.

19. The method of claim 17, wherein the first surface is the front of the substrate and the second surface is the back of the substrate or a sample attached to or near the back of the substrate.

20. An apparatus for obtaining depth-resolved spectra of a sample in order to determine the size and depth characteristics of scatterers within the sample, comprising:

[a sample that receives a sample beam and reflects a reflected sample beam in response, wherein the reflected sample beam contains light scattered from the sample;]

a receiver [that is fixed with respect] *adapted* to [the sample, that receives] *receive* a [reflected] reference beam and [the reflected] *a scattered* sample beam [and cross-correlates] *containing light scattered from a sample in response to the sample receiving a sample beam, wherein the receiver is further adapted to cross-correlate* the [reflected] reference beam with the [reflected] *scattered* sample beam;

a detector [that] *adapted to* spectrally [disperses] *disperse* the cross-correlated [reflected] reference beam and [reflected] *scattered* sample beam to yield a single [spectrally dispersed,] *spectrally-resolved* cross-correlated reflection profile having depth-resolved information about the [reflected] *scattered* sample beam; and a processor unit adapted to[:] generate a spectroscopic depth-resolved reflection profile[, by processing the single spectrally-resolved cross-correlated reflection profile by: at a plurality] *that includes characteristics* of [different center wavelengths, applying a window to] *scatterers within the sample by:*

*providing one or more spectral windows of* the single spectrally-resolved cross-correlated reflection profile*, each of the one or more spectral windows* at a given center wavelength to obtain spectral information [at the given center wavelength] *about the sample for each of the one or more spectral windows*; and

[converting] *applying a Fourier transform to* the spectral information [via Fourier transform] to recover [depth-resolved spectral] *depth* information about the sample at [all] *each given* center [wavelengths] *wavelength* simultaneously.

21. The apparatus of claim 20, wherein the processor unit is further adapted to recover size information about the sample from the spectroscopic depth-resolved reflection profile.

22. The apparatus of claim 20, wherein the processor unit is further adapted to recover [the] size information by measuring a frequency of a spectral modulation in the spectroscopic depth-resolved reflection profile.

23. The apparatus of claim 20, *wherein* the processor unit is further adapted to recover the size information by [comparing the spectroscopic depth-resolved reflection profile to a predicted analytical or numerical scattering distribution of the sample] *measuring a frequency of a spectral modulation in the spectroscopic depth-resolved reflection profile*.

24. The apparatus of claim 20, wherein [applying a processing algorithm] *providing one or more spectral windows* is comprised of [applying a] *providing one or more* Gaussian [window] *windows*, *one or more* multiple simultaneous windows, or *one or more* other window.

25. The apparatus of claim 20, wherein the receiver is comprised of a splitter.

26. The apparatus of claim 25, wherein the splitter is comprised from the group consisting of a beam splitter and an optical fiber splitter.

27. The apparatus of claim 20, wherein the sample beam comprises a collimated beam.

28. The apparatus of claim 20, wherein the [reflected] reference beam comprises a collimated beam.

29. The apparatus of claim 20, wherein the received beam is comprised of a light comprised from the group consisting of a white light generated by an arc lamp or thermal source.

30. The apparatus of claim 20, wherein the length of the path of the reference beam is fixed.

31. The apparatus of claim 20, wherein the receiver is attached to a fixed reference arm.

32. The apparatus of claim 20, wherein the sample is attached to a fixed sample arm.

33. The apparatus of claim 20, wherein the detector is comprised of a dispersive element.

34. The apparatus of claim 33, wherein the dispersive element is a spectrograph.

35. An apparatus for obtaining depth-resolved spectra of a sample comprised of a substrate having a first surface and a second surface in order to determine the size and depth characteristics of scatterers within the sample, comprising:

[a sample that receives a sample beam and reflects a first and second reflected sample beam in response, wherein the first reflected sample beam is comprised of a first portion of light scattered from the first surface of the sample, and where the second reflected sample beam is comprised of a second portion of light scattered from the second surface of the sample;]

a receiver [that is fixed with respect to the sample, that receives] *adapted to receive* a [reflected] reference beam [and the] *, a* first *scattered sample beam containing light scattered from a first surface in response to the first surface receiving a sample beam,* and *a* second [reflected] *scattered* sample [beams] *beam containing light scattered from a second surface in response to the first surface receiving a sample beam,* and [cross-correlates] *cross-correlate* the [reflected] reference beam with the first [reflected] *scattered* sample beam, and the [reflected] reference beam with the second [reflected] *scattered* sample beam;

a detector [that] *adapted to* spectrally [disperses] *disperse* the cross-correlated [reflected] reference beam and *the* first [reflected] *scattered* sample beam to yield a *first* single [first spectrally dispersed,] *spectrally-resolved* cross-correlated reflection profile having depth-resolved information about the first surface, and spectrally [disperses] *disperse* the cross-correlated [reflected] reference beam and *the* second [reflected] *scattered* sample beam to yield a *second* single [second spectrally dispersed,] *spectrally-resolved* cross-correlated reflection profile having depth-resolved information about the second surface; and a processor unit adapted to:

generate a first spectroscopic depth-resolved reflection profile[, by processing the single first cross-correlated reflection profile by, at a plurality of different center wavelengths:] *that includes characteristics of scatterers within the sample by:*

[applying a window to the] *providing one or more first spectral windows of the first* single [first] *spectrally-resolved* cross-correlated reflection profile, *each of the one or more first spectral windows* at a given center wavelength to obtain [spectral information at the given center wavelength; and converting the spectral information via Fourier transform to recover depth-resolved] *first* spectral information about the first surface of the [sample at all center wavelengths simultaneously] *substrate for each of the one or more first spectral windows*; and

*applying a Fourier transform to the first spectral information to recover depth information about the first surface at each given center wavelength simultaneously; and* generate a second spectroscopic depth-resolved reflection profile[.] *that includes characteristics of scatterers within the sample as a function wavelength and depth* by [processing the single]*:*

*providing one or more* second [cross-correlated reflection profile by:

at a plurality of different center wavelengths, applying a window to the single] *spectral windows of the* second *single spectrally-resolved* cross-correlated reflection profile, *each of the one or more second spectral windows* at a given center wavelength to obtain *second* spectral information [at the given center wavelength] *about the second surface of the substrate for each of the one or more second spectral windows*; and

[converting the spectral information via] *applying a* Fourier transform to *the second spectral information to* recover [depth-resolved spectral] *depth* information about the second surface [of the sample] at [all] *each given* center [wavelengths] *wavelength* simultaneously.

36. The apparatus of claim 35, wherein the processor unit is further adapted to recover size information about the sample by determining a ratio of the first spectroscopic depth-resolved reflection profile and the second spectroscopic depth-resolved reflection profile.

37. The apparatus of claim 35, wherein the first surface is the front of the substrate and the second surface is the back of the substrate or a sample attached to or near the back of the substrate.

*38. The method of claim 1, comprising:*

*providing the one or more spectral windows to the single spectrally-resolved cross-correlated reflection profile as a plurality of spectral windows at a plurality of different center wavelengths to obtain the spectral information for each of the one or more spectral windows; and*

*applying the Fourier transform to the spectral information to recover the depth-resolved information about the sample at all of the plurality of different center wavelengths simultaneously.*

*39. The method of claim 17, comprising:*

*providing the one or more first spectral windows to the first single spectrally-resolved cross-correlated reflection profile as a plurality of spectral windows at a plurality of different center wavelengths to obtain the first spectral information for each of the plurality of spectral windows; and*

*applying the Fourier transform to the first spectral information to recover the depth-resolved information about the first surface of the substrate at all of the plurality of different center wavelengths simultaneously.*

*40. The method of claim 17, comprising:*

*providing the one or more second spectral windows to the second single spectrally-resolved cross-correlated reflection profile as a plurality of spectral windows at a plurality of different center wavelengths to obtain the second spectral information for each of the plurality of spectral windows; and*

*applying the Fourier transform to the second spectral information to recover the depth-resolved information about the second surface of the substrate at all of the plurality of different center wavelengths simultaneously.*

*41. The method of claim 17, comprising:*

*providing the one or more first spectral windows to the first single spectrally-resolved cross-correlated reflection profile as a plurality of first spectral windows at a plurality of different center wavelengths to obtain the first spectral information for each of the plurality of first spectral windows;*

*providing the one or more second spectral windows to the second single spectrally-resolved cross-correlated profile as a plurality of second spectral windows at the plurality of different center wavelengths to obtain the second spectral information for each of the plurality of second spectral windows;*

*applying the Fourier transform to the first spectral information to recover the depth-resolved information about the first surface of the substrate at all of the plurality of different center wavelengths simultaneously; and*

*applying the Fourier transform to the second spectral information to recover the depth-resolved information about the second surface of the substrate at all of the plurality of different center wavelengths simultaneously.*

*42. The apparatus of claim 20, wherein the processor unit is adapted to:*

*provide the one or more spectral windows to the single spectrally-resolved cross-correlated reflection profile as a plurality of spectral windows at a plurality of different center wavelengths to obtain the spectral information for each of the plurality of spectral windows; and*

*apply the Fourier transform to the spectral information to recover the depth-resolved information about the sample at all of the plurality of different center wavelengths simultaneously.*

*43. The apparatus of claim 35, wherein the processor unit is adapted to:*

*provide the one or more first spectral windows to the first single spectrally-resolved cross-correlated reflection profile as a plurality of spectral windows at a plurality of different center wavelengths to obtain the first spectral information for each of the plurality of spectral windows; and*

*apply the Fourier transform to the first spectral information to recover the depth-resolved information about the first surface of the substrate at all of the plurality of different center wavelengths simultaneously.*

*44. The apparatus of claim 35, wherein the processor unit is further adapted to:*

*provide the one or more second spectral windows to the second single spectrally-resolved cross-correlated reflection profile as a plurality of spectral windows at a plurality of different center wavelengths to obtain the second spectral information for each of the plurality of spectral windows; and*

*apply the Fourier transform to the second spectral information to recover the depth-resolved information about the second surface of the substrate at all of the plurality of different center wavelengths simultaneously.*

*45. The method of claim 2, in which the scatterers are cell nuclei.*

*46. The method of claim 3, in which the scatterers are cell nuclei.*

*47. The method of claim 4, in which the scatterers are cell nuclei.*

*48. The method of claim 21, in which the scatterers are cell nuclei.*

*49. The method of claim 22, in which the scatterers are cell nuclei.*

*50. The method of claim 23, in which the scatterers are cell nuclei.*

*51. The method of claim 1, wherein the bandwidth of at least one of the one or more spectral windows is between approximately 4.4 nm and 21.0 nm.*

*52. The method of claim 1, wherein the bandwidth of each of the one or more spectral windows is between approximately 4.4 nm and 21.0 nm.*

*53. The method of claim 17, wherein the bandwidth of at least one of the one or more spectral windows of the first single spectrally-resolved cross-correlated reflection profile is between approximately 4.4 nm and 21.0 nm.*

*54. The method of claim 17, wherein the bandwidth of at least one of the one or more spectral windows of the second single spectrally-resolved cross-correlated reflection profile is between approximately 4.4 nm and 21.0 nm.*

*55. The method of claim 48, wherein the bandwidth of at least one of the one or more spectral windows of the first single spectrally-resolved cross-correlated reflection profile is between approximately 4.4 nm and 21.0 nm.*

*56. The method of claim 17, wherein the bandwidth of each of the one or more spectral windows of the first single spectrally-resolved cross-correlated reflection profile is between approximately 4.4 nm and 21.0 nm.*

*57. The method of claim 17, wherein the bandwidth of each of the one or more spectral windows of the second single spectrally-resolved cross-correlated reflection profile is between approximately 4.4 nm and 21.0 nm.*

*58. The apparatus of claim 20, wherein the bandwidth of at least one of the one or more spectral windows is between approximately 4.4 nm and 21.0 nm.*

*59. The apparatus of claim 20, wherein the bandwidth of each of the one or more spectral windows is between approximately 4.4 nm and 21.0 nm.*

*60. The apparatus of claim 35, wherein the bandwidth of at least one of the one or more spectral windows of the first single spectrally-resolved cross-correlated reflection profile is between approximately 4.4 nm and 21.0 nm.*

*61. The apparatus of claim 35, wherein the bandwidth of at least one of the one or more spectral windows of the second single spectrally-resolved cross-correlated reflection profile is between approximately 4.4 nm and 21.0 nm.*

*62. The apparatus of claim 61, wherein the bandwidth of at least one of the one or more spectral windows of the first single spectrally-resolved cross-correlated reflection profile is between approximately 4.4 nm and 21.0 nm.*

*63. The apparatus of claim 35, wherein the bandwidth of each of the one or more spectral windows of the first single spectrally-resolved cross-correlated reflection profile is between approximately 4.4 nm and 21.0 nm.*

*64. The apparatus of claim 35, wherein the bandwidth of each of the one or more spectral windows of the second single spectrally-resolved cross-correlated reflection profile is between approximately 4.4 nm and 21.0 nm.*

* * * * *

UNITED STATES PATENT AND TRADEMARK OFFICE

CERTIFICATE OF CORRECTION

PATENT NO. : RE42,497 E
APPLICATION NO. : 12/205248
DATED : June 28, 2011
INVENTOR(S) : Wax It is certified that error appears in the above-identified patent and that said Letters Patent is hereby corrected as shown below:

Claim 17, at column 11, line 4, change “first” to --second--.

Claim 55, at column 16, line 1, change “48” to --54--.

Signed and Sealed this
Twentieth Day of September, 2011

David J. Kappos

David J. Kappos
*Director of the United States Patent and Trademark Office*